US010940227B2

(12) United States Patent
Ruiz Ballesteros et al.

(10) Patent No.: US 10,940,227 B2
(45) Date of Patent: Mar. 9, 2021

(54) DEVICE FOR EVAPORATING VOLATILE SUBSTANCES

(71) Applicant: ZOBELE ESPANA, S. A., Barcelona (ES)

(72) Inventors: Julio Cesar Ruiz Ballesteros, Barcelona (ES); Fernando Mayor Sans, Barcelona (ES); Ruben Garcia Fabregas, Barcelona (ES)

(73) Assignee: ZOBELE ESPANA, S. A., Barcelona (ES)

( * ) Notice: Subject to any disclaimer, the term of this patent is extended or adjusted under 35 U.S.C. 154(b) by 0 days.

(21) Appl. No.: 15/504,401

(22) PCT Filed: Aug. 4, 2015

(86) PCT No.: PCT/ES2015/070611
§ 371 (c)(1),
(2) Date: Feb. 16, 2017

(87) PCT Pub. No.: WO2016/026993
PCT Pub. Date: Feb. 25, 2016

(65) Prior Publication Data
US 2017/0232129 A1 Aug. 17, 2017

(30) Foreign Application Priority Data
Aug. 19, 2014 (ES) .................................. 201431236

(51) Int. Cl.
*A61L 9/12* (2006.01)
*A01M 1/20* (2006.01)
(Continued)

(52) U.S. Cl.
CPC ............... *A61L 9/127* (2013.01); *A01M 1/20* (2013.01); *A01M 1/2044* (2013.01); *A61L 9/02* (2013.01); *A61L 9/04* (2013.01)

(58) Field of Classification Search
CPC . A61L 9/12; A61L 9/129; A61L 9/037; A61L 9/02; A61L 9/04; A61L 9/127; A01M 1/2044; A01M 1/20
(Continued)

(56) References Cited

U.S. PATENT DOCUMENTS

| 4,165,835 A | 8/1979 | Dearling |
| 4,544,592 A | 10/1985 | Spector |

(Continued)

FOREIGN PATENT DOCUMENTS

WO    2013014078    1/2013

OTHER PUBLICATIONS

International Search Report for PCT Application No. PCT/ES2015/070611 dated Oct. 9, 2015.
(Continued)

*Primary Examiner* — Joseph A Greenlund
(74) *Attorney, Agent, or Firm* — Kunzler Bean & Adamson

(57) ABSTRACT

The invention relates to an evaporation device for evaporating volatile substances, comprising a container (1) housing a liquid (8) containing the volatile substances, an outlet (2) through which the volatile substances exit and a hole (9) for equalizing the pressure between the inside and the outside of the container, and characterized in that it also comprises a membrane (6) placed between the container (1) and the hole (9), said membrane (6) being leak-tight with respect to said liquid (8) and porous with respect to the gases.
This membrane prevents the liquid from accidentally spilling and furthermore solves the issue of balancing pressures inside the container, keeping the rate of evaporation constant until running out of the volatile substances.

6 Claims, 2 Drawing Sheets

(51) Int. Cl.
*A61L 9/04* (2006.01)
*A61L 9/02* (2006.01)

(58) Field of Classification Search
USPC .................................................. 239/34, 57, 4
See application file for complete search history.

(56) References Cited

U.S. PATENT DOCUMENTS

| | | | | | |
|---|---|---|---|---|---|
| 4,753,389 | A | * | 6/1988 | Davis | A61L 9/01 |
| | | | | | 239/56 |
| 4,915,301 | A | * | 4/1990 | Munteanu | A61L 9/01 |
| | | | | | 239/45 |
| 4,917,301 | A | * | 4/1990 | Munteanu | A61L 9/01 |
| | | | | | 239/43 |
| 4,948,047 | A | * | 8/1990 | Zembrodt | A61L 9/01 |
| | | | | | 239/34 |
| 5,121,881 | A | * | 6/1992 | Lembeck | A61L 9/127 |
| | | | | | 239/34 |
| 5,354,133 | A | * | 10/1994 | Rapparini | B65D 77/225 |
| | | | | | 137/246 |
| 5,749,519 | A | * | 5/1998 | Miller | A61L 9/01 |
| | | | | | 239/34 |
| 6,109,537 | A | | 8/2000 | Heath | |
| 6,341,732 | B1 | * | 1/2002 | Martin | B05B 17/0646 |
| | | | | | 128/200.16 |
| 6,460,738 | B1 | * | 10/2002 | Petit | B05B 11/305 |
| | | | | | 222/189.09 |
| 6,568,557 | B2 | * | 5/2003 | Fusco | A47G 19/2272 |
| | | | | | 215/11.5 |
| 6,569,387 | B1 | * | 5/2003 | Furner | A01M 1/2033 |
| | | | | | 222/183 |
| 6,899,280 | B2 | * | 5/2005 | Kotary | A01M 1/2044 |
| | | | | | 239/34 |
| 7,303,143 | B2 | * | 12/2007 | Davis | A01M 1/2077 |
| | | | | | 239/145 |
| 7,389,943 | B2 | * | 6/2008 | Jaworski | A01M 1/205 |
| | | | | | 239/102.2 |
| 7,824,627 | B2 | * | 11/2010 | Michaels | B05B 17/0646 |
| | | | | | 422/128 |
| 7,920,777 | B2 | * | 4/2011 | Rabin | A61M 16/021 |
| | | | | | 392/396 |
| 7,959,035 | B2 | * | 6/2011 | Pruvot | B05B 11/3047 |
| | | | | | 222/189.09 |
| 7,997,508 | B2 | * | 8/2011 | Motylinski | A61L 9/127 |
| | | | | | 239/6 |
| 8,677,679 | B2 | * | 3/2014 | Black | A01M 1/2033 |
| | | | | | 239/44 |
| 9,173,389 | B2 | * | 11/2015 | Boyd | A01M 29/12 |
| 9,185,897 | B2 | * | 11/2015 | Boyd | A01M 29/12 |
| 9,254,063 | B2 | * | 2/2016 | Libourel | A47J 41/02 |
| 9,987,386 | B2 | * | 6/2018 | Tsurumi | A01M 1/2044 |
| 2004/0118936 | A1 | * | 6/2004 | Schram | B05B 17/0607 |
| | | | | | 239/145 |
| 2004/0256310 | A1 | * | 12/2004 | Cheng | B01D 67/0009 |
| | | | | | 210/490 |
| 2006/0255075 | A1 | * | 11/2006 | Foster | B05B 11/0044 |
| | | | | | 222/383.1 |
| 2008/0276523 | A1 | | 11/2008 | McKechnie | |
| 2009/0101730 | A1 | * | 4/2009 | Davis | A61L 9/037 |
| | | | | | 239/44 |
| 2011/0072711 | A1 | | 3/2011 | Black et al. | |
| 2012/0126024 | A1 | * | 5/2012 | Boyd | A01M 1/2044 |
| | | | | | 239/6 |
| 2014/0140683 | A1 | * | 5/2014 | Stephenson | A61L 9/037 |
| | | | | | 392/395 |
| 2017/0232129 | A1 | * | 8/2017 | Ruiz Ballesteros | A61L 9/02 |
| | | | | | 239/34 |

OTHER PUBLICATIONS

Extended European Search Report for EP Patent Application No. 15832989.6 dated Feb. 27, 2018.

* cited by examiner

DEVICE FOR EVAPORATING VOLATILE SUBSTANCES

The present invention relates to an evaporation device for evaporating volatile substances comprising an improved vacuum compensation system provided with a microporous membrane.

BACKGROUND OF THE INVENTION

The use of membranes that are porous with respect to the air is well-known on the market and applied in products containing chemical substances. These membranes act like exhaust valves, allowing the exit of gases from the volatile substance stored inside a container and preventing an excess pressure from occurring inside the product container.

The generation of gases by volatile substances basically occurs during storage of the container and as a result of the increase in temperature of the surrounding area, and it requires using a pressure compensation system.

A hole communicating the fragrance contained in the bottle with the exterior has conventionally been used as a pressure compensation system in air freshening products or insecticides comprising a bottle with wick and fragrance (liquid air freshener or insecticide).

The pressure compensation hole is useful because the pressure inside the bottle must be balanced with the exterior, because otherwise, as a result of the evaporation of the liquid, negative pressure (in relative terms) would be generated inside the container, whereby evaporation would be slower, even stopping.

A serious drawback to using this hole is that an open system is created during use of the air freshener or insecticide by the user, so it is susceptible to fragrance spilling out through the hole as a result of the container accidentally tipping over.

Therefore, the need for a leak-tight pressure compensation system such that it does not allow the liquid to exit, even if the container were accidentally tipped over.

DESCRIPTION OF THE INVENTION

The mentioned drawbacks are solved with the evaporation device for evaporating volatile substances of the invention, having other advantages that will be described below.

The evaporation device for evaporating volatile substances according to the present invention comprises a container housing a liquid containing the volatile substances, an outlet through which the volatile substances exit and a hole for equalizing the pressure between the inside and the outside of the container, and it is characterized in that it also comprises a membrane placed between the container and the hole, which is leak-tight with respect to said liquid and porous with respect to the gases, allowing said volatile substances to exit and air to enter.

According to a preferred embodiment, said membrane is microporous and made of polytetrafluoroethylene, although it could also be made of any material that is leak-tight with respect to the liquid and porous with respect to the gases in a two-way manner, such as polypropylenes and polyethylenes microporous.

Advantageously, said membrane is mounted in a casing, which is preferably made of a plastic material.

Furthermore, said hole is preferably defined in a plug closing said container, and said casing is mounted inside said plug.

Said hole is advantageously closed by a cover before the first use of the device to prevent the volatile substances from coming out. Said cover can be a stopper or a sheet material that are removed right before the first use of the device according to the present invention.

The use of a membrane made of a porous material as a pressure compensation system generates a closed system, i.e., leak-tight with respect to the liquid. As the membrane allows air to enter but does not allow the liquid to exit, the use of the membrane solves the two issues inherent to system functionality.

On one hand, it prevents the liquid from accidentally spilling and further solves the issue of balancing pressures inside the container. It allows air to enter same and it allows keeping the rate of evaporation constant until the volatile substances run out.

It is evident that since air is left to get through, the membrane will also leave the vapors of the volatile substance to get out of the container. In order to prevent this phenomenon from interfering with controlled evaporation through the main outlet, the outwardly opening surface area of the hole will be kept below 5% of the main evaporation surface (wick).

BRIEF DESCRIPTION OF THE DRAWINGS

To better understand the preceding description, several drawings are attached which schematically depict a practical embodiment by way of non-limiting example.

DESCRIPTION OF A PREFERRED EMBODIMENT

Figure 1:
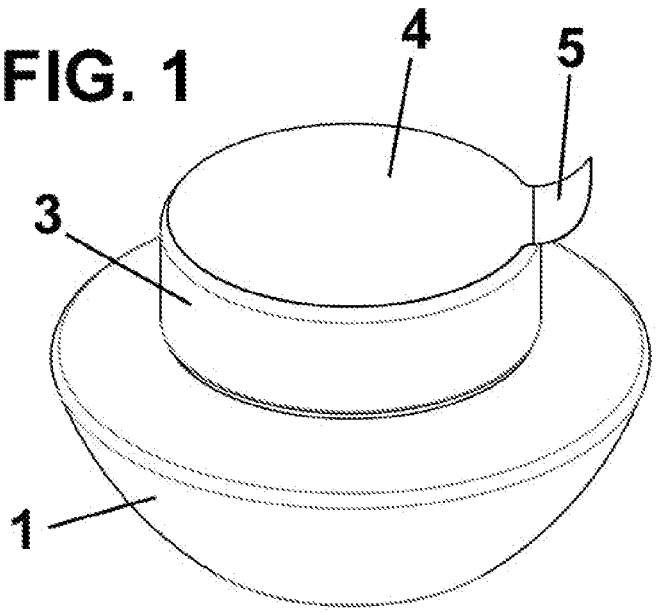
FIG. 1 is a perspective view of the evaporation device for evaporating volatile substances according to the present invention, in its position before the first use.
Figure 2:
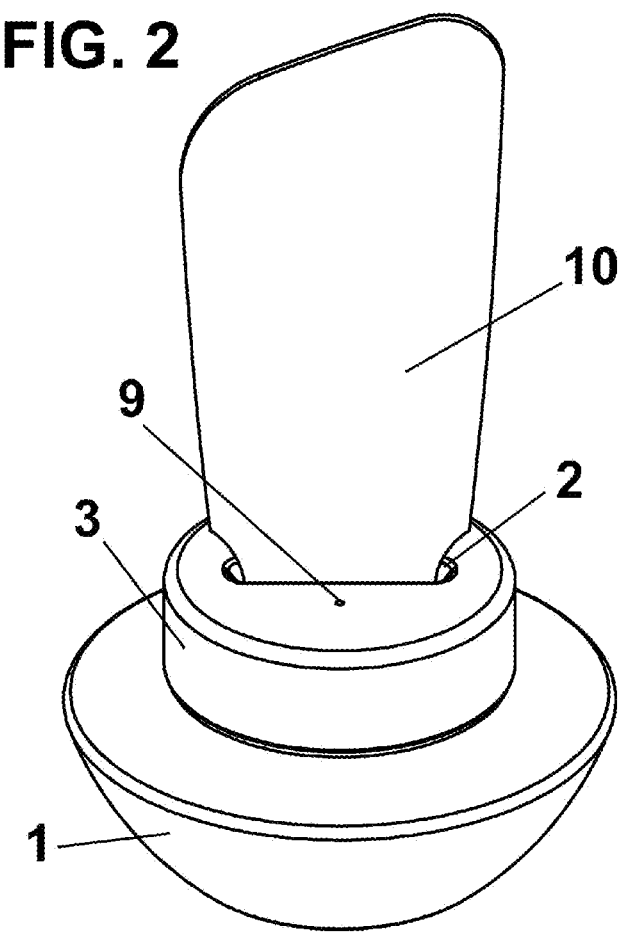
FIG. 2 is a perspective view of the evaporation device for evaporating volatile substances according to the present invention, during use.

The evaporation device for evaporating volatile substances according to the present invention comprises a container 1 housing a liquid 8 containing said volatile substances which will be evaporated out into the environment, preferably in a passive manner, through an outlet 2 defined in a plug 3. Preferably, said outlet 2 is provided with a wick 10 so that the volatile substances are evaporated as intended.

To prevent the volatile substances to exit during storage of the device of the present invention before the first use, said outlet 2 is closed by means of a cover 4, such as a sheet material, as can be seen in FIG. 1, or by means of any suitable closure element, for example a stopper or the like.

In the event of using a sheet material, it can be made of aluminum and be welded or adhered onto the plug 3, closing the outlet 2. In order to make it easier to remove the sheet material, it can comprise a tab 5, as seen in FIG. 1.

Furthermore, the evaporation device for evaporating volatile substances also comprises a hole 9 for equalizing the pressure between the inside and the outside of the container, each membrane 6 being placed between the container 1 and the hole 2, said membrane 6 being leak-tight with respect to said liquid and porous with respect to the gases, allowing said volatile substances to exit and allowing air to enter from the outside. This hole 9 will also be closed by said cover 4 before the first use of the evaporation device.

Figure 3:
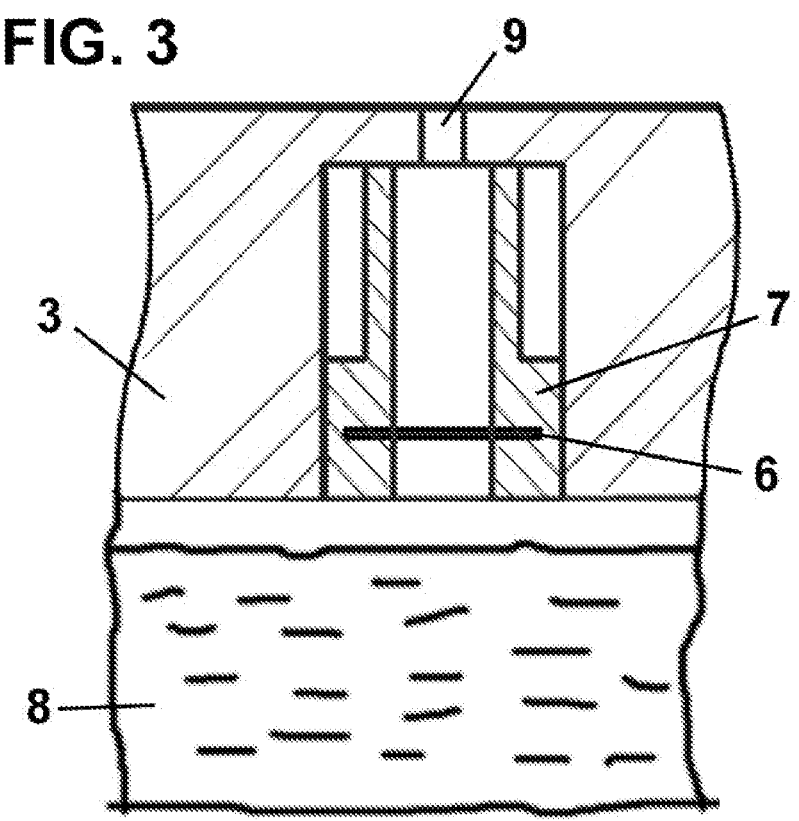
FIG. 3 is a section view of the central part of the evaporation device for evaporating volatile substances according to the present invention.

As can be seen in FIG. 3, this membrane 6 is preferably mounted in a casing 7, which is in turn placed inside the plug 3. Both the casing 7 and the plug 3 are preferably made of plastic material, although they could be made of any suitable material.

According to a preferred embodiment, the membrane 6 is made of polytetrafluoroethylene, although it could be made of any other suitable material allowing it to be leak-tight with respect to the liquid but porous with respect to the gases in a two-way manner.

The porous membrane 6 also has the following technical features:

The membrane 6 has a resistance against water going through same, measured in terms of pressure, greater than 0.3 bar.

The nominal airflow is at least 0.1 l/h.

The working temperature range of the membrane 6 is from −40° C. to 120° C.

The general diameter of the casing of the membrane is greater than 3 mm in diameter.

The operation of the evaporation device for evaporating volatile substances according to the present invention is as follows:

When the evaporation device is to be used for the first time, the cover 4 will have to be removed, which can be done by simply pulling on the tab 5. The user will then have to insert the wick into the outlet 2.

By removing the cover 4, volatile substances contained in the liquid 8 will be allowed to exit through the outlet 2 by means of the wick 10. Furthermore, air will also be allowed to enter into the container 1, going through the membrane 6 arranged in the hole 9, for equalizing the pressures on the inside and on the outside of the container 1, as a result of the gas permeability of the membrane 6.

However, leak-tightness with respect to the liquid of the evaporation device is assured as a result of the feature of the membrane 6 that prevents the liquid from passing through said membrane 6.

In an alternative embodiment, the cover 4 may be applied on just the hole 9 and not on the outlet 2.

Although the described system is designed to be a passive system, releasing the volatile substances without the action of another element, it could obviously be used with other known evaporation systems such as heating elements, fans, etc.

Despite having made reference to a specific embodiment of the invention, it is obvious for a person skilled in the art that the described evaporation device for evaporating volatile substances is susceptible to a number of variations and modifications, and that all the mentioned details can be replaced with other technically equivalent details without departing from the scope of protection defined by the attached claims.

The invention claimed is:

1. An evaporation device for evaporating volatile substances, comprising a container housing a liquid containing the volatile substances, an outlet through which the volatile substances exit and a hole for equalizing the pressure between the inside and the outside of the container, characterized in that the evaporation device also comprises:
   a plug closing said container, wherein the outlet and the hole are formed in the plug;
   a wick extending through the outlet, such that the wick is secured by the plug, and into contact with the liquid in the container, and wherein the volatile substances exit the container through the outlet via the wick;
   a casing mounted inside the plug, such that the casing is separate from and mounted to the plug; and
   a membrane placed between the container and only the hole such that the membrane is not placed between the container and the outlet, said membrane being leak-tight with respect to said liquid and porous with respect to air to allow air to enter the container through the hole as the volatile substances exit the container through the outlet via the wick gases, wherein the membrane is permeable to gas such that air can enter the container through the hole and exit the container through the hole;
   wherein the membrane is mounted to and inside the casing, such that the casing and the membrane form a unit that is separate from the plug and such that, when the casing is mounted inside the plug, the membrane is spatially offset from the hole.

2. The evaporation device for evaporating volatile substances according to claim 1, wherein said membrane is microporous.

3. The evaporation device for evaporating volatile substances according to claim 1, wherein said membrane is made of polytetrafluoroethylene, polypropylene or polyethylene.

4. The evaporation device for evaporating volatile substances according to claim 1, wherein said hole is closed by means of a cover before the first use of the device.

5. The evaporation device for evaporating volatile substances according to claim 4, wherein said cover is a stopper or a sheet material.

6. The evaporation device for evaporating volatile substances according to claim 1, wherein an outwardly opening surface area of the hole is less than 5% of an evaporation surface area of the wick.

* * * * *